United States Patent [19]

Griffith et al.

[11] Patent Number: 5,354,996
[45] Date of Patent: Oct. 11, 1994

[54] METAL ION MONITORING SYSTEM

[75] Inventors: Jeffrey K. Griffith, Cedar Crest; Teresa A. Coons; Jack E. Floegel, both of Albuquerque, all of N. Mex.

[73] Assignee: Permacharge Corporation, Albuquerque, N. Mex.

[21] Appl. No.: 80,293

[22] Filed: Jun. 21, 1993

[51] Int. Cl.$^5$ ............................................. C02F 1/42
[52] U.S. Cl. .................................. 250/364; 250/432 B; 210/660; 210/682; 210/688
[58] Field of Search .................. 250/304, 432 R, 435, 250/364; 210/96.1, 739, 660, 682, 688

[56] References Cited

U.S. PATENT DOCUMENTS

| | | | |
|---|---|---|---|
| 3,617,563 | 11/1971 | Fuxelius | 210/688 |
| 4,070,281 | 1/1978 | Tagashira et al. | 210/664 |
| 4,343,706 | 8/1982 | Etzel et al. | 210/667 |
| 4,587,543 | 5/1986 | Ohtani et al. | 257/253 |
| 4,737,465 | 4/1988 | Bond et al. | 210/659 |
| 4,747,949 | 5/1988 | Barkey | 210/688 |
| 4,886,598 | 12/1989 | Barkey | 210/263 |
| 5,010,181 | 4/1991 | Coughlin | 210/668 |

*Primary Examiner*—Paul M. Dzierzynski
*Assistant Examiner*—Drew A. Dunn
*Attorney, Agent, or Firm*—McCubbrey, Bartels & Ward

[57] ABSTRACT

A metal ion detection and quantification system in which the displacement of a radioactive isotope from a material that binds both the metal ion of interest and the radioactive isotope. The material in question binds the radioactive isotope with less force than the isotope of interest. The extent of release of the radioactive isotope is used to determine the concentration of the metal ion of interest. In one embodiment of the invention, the material used to bind the metal ion and radioactive ion is a protein of the metallothionein class of proteins.

16 Claims, 4 Drawing Sheets

METAL ION MONITORING SYSTEM

FIELD OF THE INVENTION

The present invention relates to metal ion detection, and more particularly, to an improved apparatus and method for detecting low levels of heavy metals.

BACKGROUND OF THE INVENTION

Heavy metal contamination is increasingly becoming recognized as a major environmental problem. Effective monitoring of releases of heavy metals poses a number of problems. Acceptable levels of heavy metals in the environment are very low for many metals; hence, very sensitive measurements must be made. Existing measurement techniques having the necessary sensitivity do not lend themselves to field conditions. Metal assays often require spectroscopic instruments that are not well suited to field use. As a result, samples must be taken, labeled with the location of the sample site, and then returned to a central laboratory for analysis. The analysis procedures typically require highly trained laboratory personnel. The need for trained personnel, expensive instrumentation, and the transportation and handling of large numbers of samples makes it difficult to provide simultaneous monitoring of a large number of sites.

In addition, the contamination of waterways and the like often results from sporadic releases. If the samples are not taken at a time that is properly correlated with that of the release, the contamination event will be missed. In principle, an ion exchange column, or the like, may be used to continuously sample the water source over a large period of time, and thereby, avoid missing the contamination event. In such systems, samples from the waterway are continuously taken and pumped through an ion exchange column. After some period of time, the column is removed and the contents analyzed for heavy metals. Unfortunately, the lifetime of an ion exchange resin in the field is quite limited. Most water sources contain naturally occurring high levels of calcium, magnesium, and/or iron. These materials rapidly saturate ion exchange resins rendering the resins incapable of collecting heavy metals. Furthermore, the continued exposure to hard water after trapping heavy metal may lead to the loss of the trapped metals by exchange reactions with the innocuous elements in the hard water. At best, an examination of the material trapped by the resin will provide information about the average levels in the body of water being sampled. As a result, a short term, high level release can be missed because the resulting concentration is below that of the measurement instruments used to analyze the material trapped on the resin.

Broadly, it is the object of the present invention to provide an improved detection system for heavy metals.

It is a further object of the present invention to provide a detection system that can be used to monitor a water source over a longer period of time than that available with existing systems.

It is a still further object of the present invention to provide a detection system that will not be swamped by innocuous background minerals that are often found in hard water sources.

It is yet another object of the present invention to provide a detection system that has greater sensitivity than existing detection systems.

These and other objects of the present invention will become apparent to those skilled in the art from the following detailed description of the invention and the accompanying drawings.

SUMMARY OF THE INVENTION

The present invention comprises an apparatus for detecting the presence of a first type of metal ion in a liquid. The apparatus includes a first compartment having bound therein a first material that binds both the first type of metal ion and a second type of metal ion, the second type of metal ion being bound with less force than the first type of metal ion. The first material has a radioactive isotope of the second type of metal ion initially bound thereto. A known volume of the liquid is brought into contact with the material in the first compartment and then the first material is isolated from the liquid. The amount of radioactivity remaining on the first material is then measured to determine the concentration of the first type of metal ion in the liquid. In one embodiment of the present invention, the liquid is caused to flow through the first compartment and then through a second compartment that contains a material that binds the second type of metal ion.

DETAILED DESCRIPTION OF THE INVENTION

The present invention is based on the observation that there are materials that selectively bind metal ions with differing degrees of affinity depending on the particular metal ion. For example, the class of proteins referred to as metallothionein binds a number of metal ions with differing affinities. For example, mammalian metallothionein binds the following metal ions, the affinity of binding being in the indicated order:

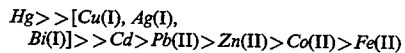

Consider the case in which a bed of metallothionein is first saturated with Cd. If the bed is exposed to Pb, Zn, or any of the other metals that are bound with less force than Cd, the Cd remains attached to the metallothionein. If, however, the bed is exposed to Hg, Cu(I), or any of the metals having higher binding constants than that of Cd, the Cd will be displaced from the bed. In addition, the ion that displaced the Cd will now be tightly bound to the metallothionein. Hence, an examination of the metallothionein bed will provide information as to which metal ion came in contact with the bed.

Figure 1:
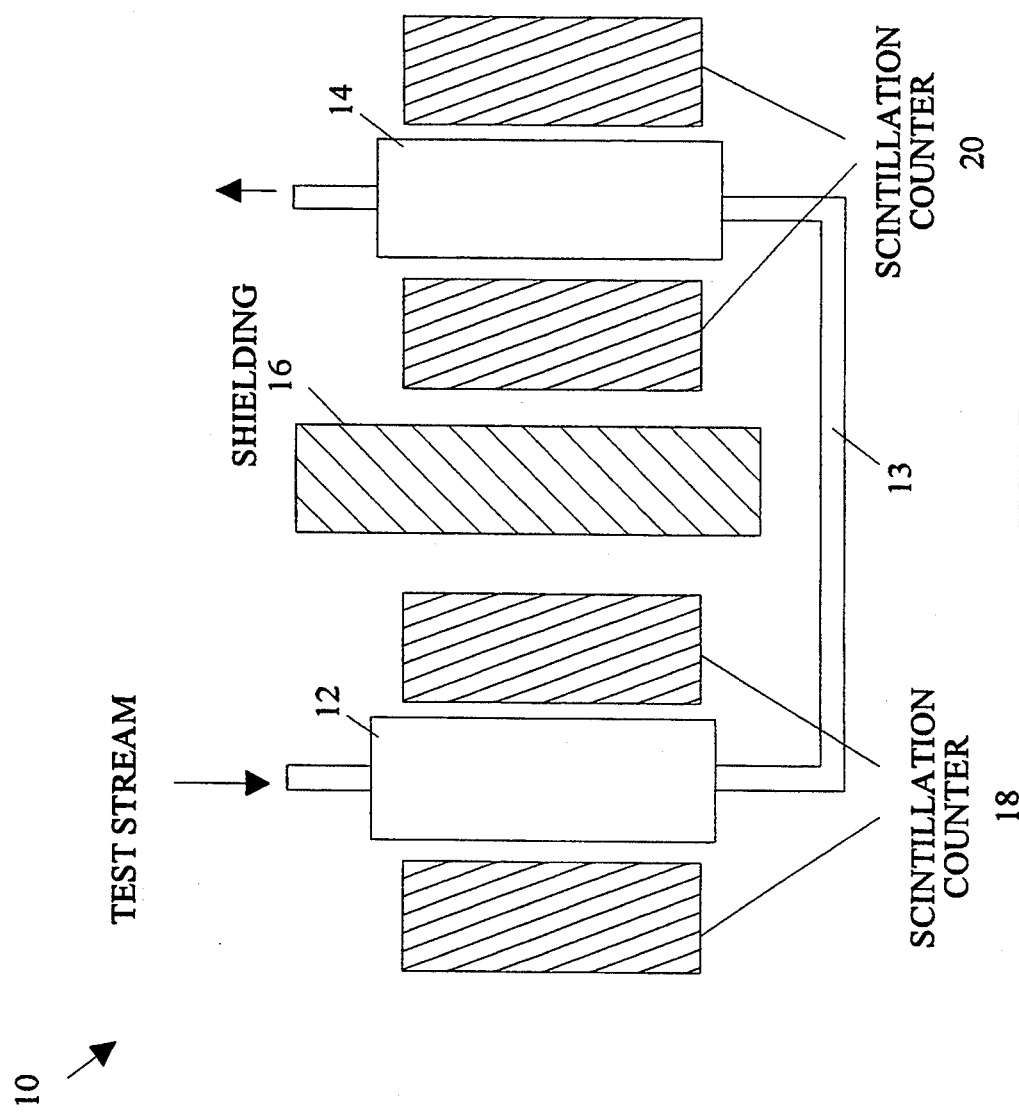
FIG. 1 is cross-sectional view of a sensor according to the present invention.

Refer now to FIG. 1 which is a cross-sectional view of a detector 10 according to the present invention which may be used to constantly monitor a test stream for metal ion contamination. Detector 10 includes two compartments 12 and 14 that are connected by a passage 13. Liquid entering compartment 12 passes through compartment 12 and into compartment 14 via passage 13. The liquid then exits compartment 14. Compartments 12 and 14 contain a metallothionein protein bound to a solid support which is sufficiently porous to allow liquid to flow therethrough. The metallothionein protein in compartment 12 is initially loaded with a radioactive metal ion having a lower binding constant than the that of metal ions that are to be detected. For example, if Hg is to be detected using the metallothionein protein described above, the metallothionein in compartment 12 may be loaded with $^{109}$Cd. The amount of radioactivity in compartment 12 is monitored by radiation detector 18.

Compartment 14 is initially loaded with metallothionein that is free of metal ions or which is loaded with metal ions having a binding constant significantly less than the binding constant of Cd. If Hg is released into the test stream, the Hg will displace some of the $^{109}$Cd from compartment 12. The released Cd will be collected by the metallothionein in compartment 14. Radiation detector 20 monitors the radioactivity of the material bound in compartment 14. Shielding wall 16 isolates radiation detector 20 from radiation detector 18.

Figure 2:
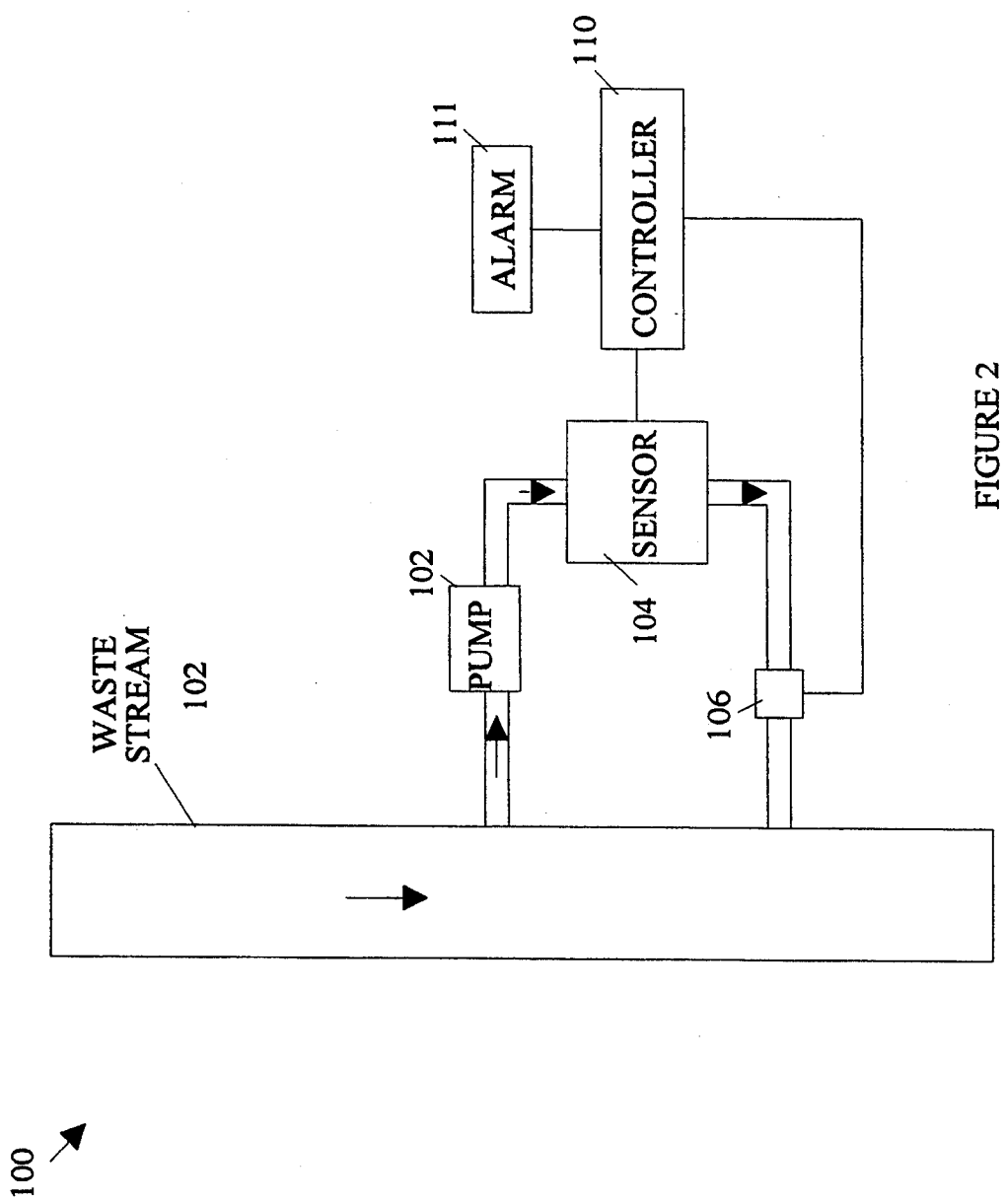
FIG. 2 illustrates the placement of a sensor according to the present invention with respect to a waste stream to be monitored.

When sufficient radioactivity has been transferred from compartment 12 to compartment 14, detector 10 is taken off-line and the contents of compartment 12 examined to determine which metal ions have been bound by the metallothionein in compartment 12. Refer now to FIG. 2 which illustrates at 100 the use of a sensor 104 constructed from a detector such as detector 10. A portion of a waste stream 102 is diverted through sensor 104 by pump 102. When sufficient radioactivity is transferred from the first compartment in sensor 104 to the second compartment, controller 110 closes valve 106 to prevent loss of radioactivity from the second compartment. At the same time, controller 110 turns off pump 102 and sounds alarm 111 to summon an operator to remove sensor 104 for examination. Controller 110 may also divert waste stream 102 to a holding tank until the source and nature of the contamination is determined.

It should be noted that the trigger point is independent of the concentration of the metal ions in the test stream. A detector according to the present invention measures the sum of the metal ions passing therethrough. Hence, the detector may be used to detect low level continuous emissions of metal ions or high levels of metal ions emitted in a short pulse. A detector according to the present invention is capable, however, of differentiating between a continuous low level of the heavy metal and a short term higher level release by continuously recording the outputs of scintillation counters 18 and 20. A short term high level release will be characterized by a rapid increase in the activity in compartment 14 coupled to a a rapid decrease in the activity in compartment 12.

In principle a detector according to the present invention may be constructed without compartment 14. Compartment 14 provides three functions. First, compartment 14 captures the radioactivity released from compartment 12. This prevents the release of radioactivity into the environment. While the amount of radioactivity in compartment 12 is too small to cause environmental or health hazards, the public's concerns over radioactive releases are such that it is advantageous to provide a means for avoiding any releases of radioactivity.

Second, by examining the rate at which radioactivity is transferred from compartment 12 to compartment 14, the nature of the metal ion releases in the test stream may be determined. When the amount of radioactivity in compartment 12 is high, it is difficult to accurately measure a small release, since the release is a small fraction of the amount of radioactivity in the compartment. In this case, compartment 14 will have very little radioactivity. Thus, an increase in radioactivity in compartment 14 will be readily detectable.

Finally, monitoring the contents of compartment 14 provides a means for assuring that the detection apparatus is functioning as designed. There are situations in which all of the radioactivity could be removed from both compartments 12 and 14 without competing metal ions being the cause of the removal. For example, if a very high concentration of acid were present in the test stream, all of the metal ions could be stripped from the metallothionein and the stripped ions would not be captured by the metallothionein in compartment 14.

Compartments 12 and 14 must pass liquid at an acceptable rate while binding the metallothionein such that it is not released from the compartments. In one embodiment of the present invention, the metallothionein is bound to acrylate beads within the compartment. Suitable porous plugs are used to confine the beads to the compartments. The beads may be prepared by incubating Affigel-10 (BioRad-Catalogue 153-6099) that has been washed in 0.1M sodium borate (pH8.5) with metallothionein and $^{109}$CdCl$_2$. In one preparation, the beads for compartment 12 were prepared by mixing one ml of Affigel-10 slurry with 50 μg of metallothionein and 0.5 μg of $^{109}$CdCl$_2$. The beads for compartment 14 are prepared by the same procedure without the $^{109}$CdCl$_2$.

If the resin is loaded with $^{109}$CDCl$_2$ having a specific activity of 1 Curie/rag, a sensor capable of detecting 1 picogram of mercury can be constructed. This would allow the detection of levels as dilute as 2 parts per billion in a waste stream.

While the above described embodiments of the present invention use $^{109}$CDCl$_2$ as the labeling material, any isotope which is bound less strongly than the metallic species of interest may be utilized. It is preferred, however, that the isotope used be a gamma-ray or neutron emitting isotope. Charged particle emitting isotopes are difficult to quantify because the range of the emitted particle is too short to allow the particle to escape from the resin.

Figure 3:
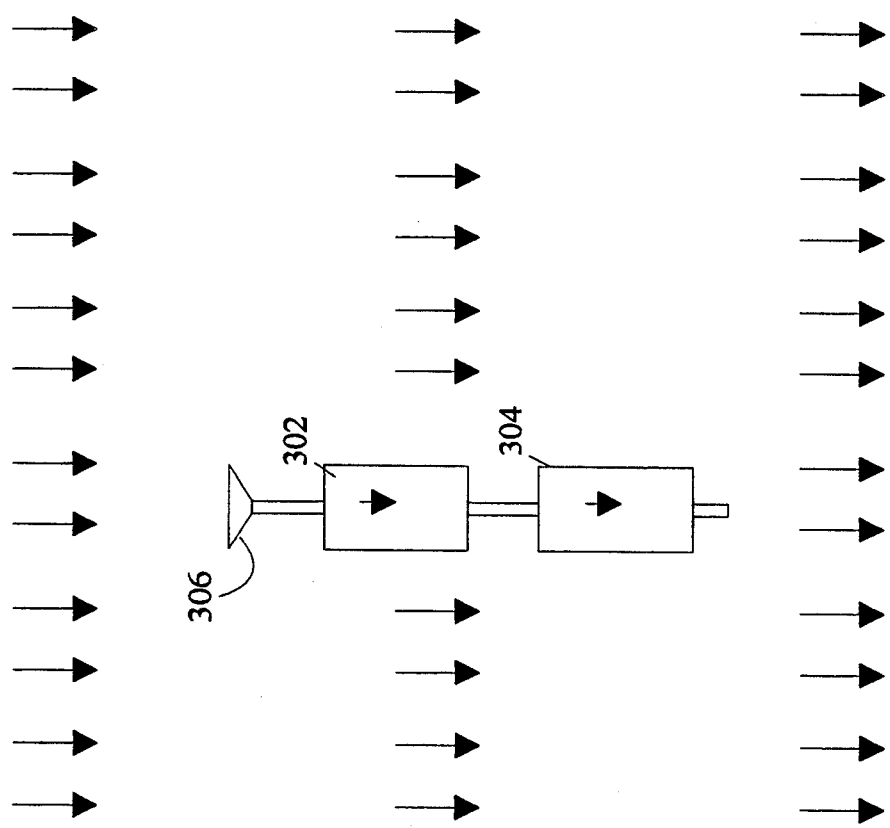
FIGS. 3 illustrates the placement of a sensor according to the present invention that does not include a radiation detector in a waste stream.

While the above described embodiments of the present invention utilize a radiation detector as part of the instrument that is placed in the field, it will be apparent to those skilled in the art that units lacking a radiation detector can be placed in the field. Referring to FIG. 3, a sensor comprising compartments 302 and 304 can be placed at a monitoring location in a manner that provides a flow of the water source through the chambers. For example, the sensor may be tethered in a flowing stream such that the flow of the stream causes water to flow through the sensor. The rate of flow can be controlled by including a funnel such as that shown at 306 on the input port of the first chamber. The sensors would then be collected at periodic intervals and taken to a central location for measurement of the radioactivity in the compartments.

The above described embodiments of the present invention utilize a material in compartment 14 that is the same as that in compartment 12 with the exception that the material is initially not loaded with any metal ion. However, it will be apparent to those skilled in the an that other materials may be used. Any material that will bind the label released from compartment 12 may be used.

While the above described embodiments of the present invention have utilized a particular metallothionein protein, it will be apparent to those skilled in the art that any metallothionein protein could be utilized. For the purposes of this discussion, the term metallothionein is defined to include any protein or series of amino acids that selectively binds at least two metal ions with binding constants that are different for the two metal ions in question. It will also be apparent to those skilled in the art that non-protein material may be used in place of the metallothionein. For example, some of the zeolites have the ability to bind metal ions with differing binding constants. It is this ability that makes these compounds good water softening agents.

Figure 4:
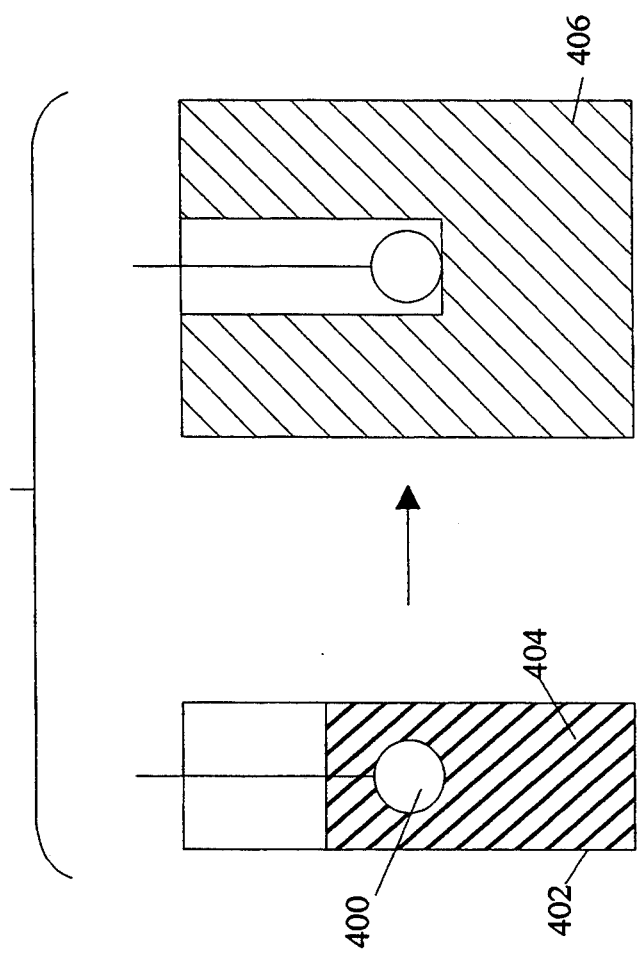
FIG. 4 illustrates the use of a porous pellet according to the present invention.

The above embodiments of the present invention operate by passing the liquid to be monitored through a chamber containing metallothionein that has been initially loaded with a radioactive isotope of a metal that is bound with less than affinity that the metal to be measured. It will be apparent to those skilled in the art that other configurations of the assay taught herein are possible. For example, the metallothionein can be bound to the pores of a porous pellet 400 as shown in FIG. 4. The metallothionein is initially loaded with the radioactive isotope. The pellet is then suspended in a container 402 of the liquid 404. After the pellet has sufficient time to equilibrate with contents of the container, the pellet is transferred to a radiation detector 406 to determine the amount of radioactivity that is still bound to the pellet.

Various modifications to the present invention will become apparent to those skilled in the art from the foregoing description and accompanying drawings. Accordingly, the present invention is to be limited solely by the scope of the following claims.

What is claimed is:

1. An apparatus for detecting the presence of a first type of metal ion in a liquid, said apparatus comprising:
   a first compartment having bound therein a first material that binds said first type of metal ion and a second type of metal ion, said second type of metal ion being bound with less force than said first type of metal ion, said first material having a radioactive isotope of said second type of metal ion initially bound thereto;
   contact means for bringing a known volume of said liquid in contact with said material in said first compartment and then isolating said first material from said liquid.

2. The apparatus of claim 1 wherein said contact means comprises means for causing said liquid to flow through said first compartment.

3. The apparatus of claim 2 further comprising a second compartment having a second material bound therein that binds said second type of metal ion, and wherein said contact means further comprises means for causing said liquid to flow through said second compartment after flowing through said first compartment.

4. The apparatus of claim 1 wherein said first compartment comprises a porous pellet having said first material bound in the pores thereof.

5. The apparatus of claim 1 wherein said first material comprises a metallothionein.

6. The apparatus of claim 1 wherein said first said material comprises a zeolite.

7. The apparatus of claim 1 further comprising means for measuring radioactivity bound to said first material after said liquid has been brought into contact with said first material in said first compartment.

8. The apparatus of claim 3 further comprising means for measuring the radioactivity in said first compartment and means for measuring the radioactivity in said second compartment.

9. A method for detecting the presence of a first type of metal ion in a liquid, said method comprising the steps of:
   bringing said liquid into contact with a first material that binds said first type of metal ion and a second type of metal ion, said second type of metal ion being bound with less force than said first type of metal ion, said first material having a radioactive isotope of said second type of metal ion initially bound thereto; and
   isolating said first material from said liquid.

10. The method of claim 9 wherein said step of bring said liquid into contact with said first material comprises causing said liquid to flow through a first compartment containing said first material.

11. The method of claim 10 further comprising the step of causing said liquid to flow through a second compartment after flowing through said first compartment, said second compartment containing a material that binds metal ions of said second type.

12. The method of claim 11 further comprising the steps of measuring the radioactivity in said first compartment and the radioactivity in said second compartment.

13. The method of claim 9 wherein said step of bringing said liquid into contact with said first material comprising immersing a porous pellet in said liquid, said porous pellet having said first material bound in the pores thereof.

14. The method of claim 9 wherein said first said material comprises a zeolite.

15. The method of claim 9 further comprising the step of measuring radioactivity bound to said first material after said liquid has been brought into contact with said first material.

16. The method of claim 9 wherein said first material comprises a metallothionein.

* * * * *